United States Patent [19]

Murata et al.

[11] 4,328,478
[45] May 4, 1982

[54] HUMIDITY SENSITIVE DEVICE

[75] Inventors: Michihiro Murata, Kyoto; Shinsei Okabe, Takatsuki, both of Japan

[73] Assignee: Murata Manufacturing Co., Ltd., Japan

[21] Appl. No.: 184,802

[22] Filed: Sep. 8, 1980

[30] Foreign Application Priority Data

Sep. 11, 1979 [JP] Japan .................................. 54/116916

[51] Int. Cl.³ .............................................. G01W 1/02
[52] U.S. Cl. ........................................ 338/35; 29/620; 73/335
[58] Field of Search ...................... 73/336.5, 336, 335; 338/35, 34; 29/620

[56] References Cited

U.S. PATENT DOCUMENTS

| 3,671,913 | 6/1972 | Mamlya et al. | 73/336.5 |
| 4,015,230 | 3/1977 | Nitta et al. | 338/35 |
| 4,086,556 | 4/1978 | Nitta et al. | 338/35 |

Primary Examiner—Donald O. Woodiel
Attorney, Agent, or Firm—Ostrolenk, Faber, Gerb & Soffen

[57] ABSTRACT

A humidity sensitive device comprises a base body of a preferably porous semiconductive ceramic having a grain boundary. A high resistance layer is formed in the grain boundary of the semiconductive ceramic and exhibits a humidity sensitive characteristic. First and second electrodes for withdrawing an electrical signal are formed spaced from each other on at least one major surface of the semiconductive ceramic base.

24 Claims, 8 Drawing Figures

HUMIDITY SENSITIVE DEVICE

BACKGROUND OF THE INVENTION

1. Field of the Invention

The present invention relates to a humidity sensitive device.

More specifically, the present invention relates to a novel humidity sensitive device mainly including semiconductive ceramics.

2. Description of the Prior Art

Generally a humidity sensitive device utilizes a property of an electrical resistance of a substance which is changeable as a function of a humidity. The characteristics required for such humidity detecting device are high reliability, a long life, a practically measurable range such as a resistance $R = 10 - 10^7 \Omega$, stability in a gas atmosphere, a relatively small temperature dependency, utilizability at a low and high temperature such as 100° C., and the like; however, present few if any humidity sensitive devices meeting such ideal conditions are available.

For example, one known humidity sensitive device utilizing organic macro molecules is unsatisfactory in reliability and life. A second known humidity sensitive device having a pair of electrodes formed on a magnetite film of $30\mu$ in thickness also has too short a life. A third humidity sensitive device of a nickel ferrite group has also been developed and announced but has not been put into practical use, because it is difficult to manufacture and mass production of good reproducibility is doubtful.

SUMMARY OF THE INVENTION

In brief, the present invention comprises a humidity sensitive device, comprising: a device body including a semiconductive ceramic having a grain boundary and having a major surface, a high resistance layer formed in the grain boundary of the semiconductive ceramic and having a humidity sensitive function, and an electrode formed on the major surface of the device body.

Preferably, the high resistance layer comprises an oxide layer obtained by oxidation of the grain boundary of the semiconductive ceramic. Preferably, the high resistance layer may comprise an impurity layer obtained through reaction of ions on the grain boundary of the semiconductive ceramic for controlling the humidity sensitive characteristic.

Since the inventive humidity sensitive device comprises a semiconductive ceramic device body, the device exhibits less time dependent deterioration of the characteristic and exhibits a relatively stable operation characteristic. Furthermore, the sensitivity and the device resistance can be changed with ease by changing the thickness of the high resistance layer formed on the grain boundary of the semiconductive ceramic and by changing the kinds of ions for reaction, which permit suitable design of the device according to the applications. Since the semiconductive ceramic itself also has an inherent resistance value, a design suitable for a given application can also be attained by changing the material of the semiconductive ceramic. Thus, the inventive device is easy to miniaturize, simple to produce and inexpensive.

Accordingly, a principal object of the present invention is to provide a humidity sensitive device which can meet various characteristics as required.

These objects and other objects, features, aspects and advantages of the present invention will become more apparent from the following detailed description of the present invention when taken in conjunction with the accompanying drawings.

DESCRIPTION OF THE PREFERRED EMBODIMENTS

The present invention comprises a humidity sensitive device, comprising: a base body including a semiconductive ceramic preferably of porosity having a grain boundary; a high resistance layer formed in the grain boundary of the semiconductive ceramic and exhibiting a humidity sensitive function; and an electrode formed on the major surface of the semiconductive ceramic base for withdrawing an output electrical signal.

Figure 1:
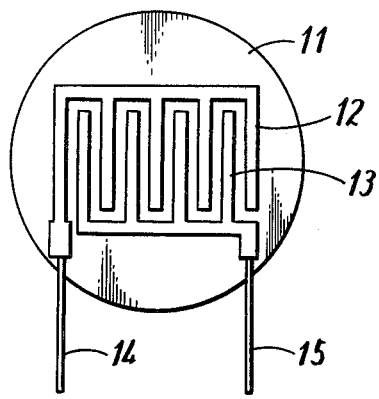
FIG. 1 is a plan view showing one example of the inventive humidity sensitive device.
Figure 2:
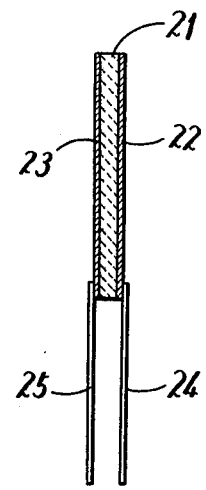
FIG. 2 is a sectional view of another embodiment of the present invention.

FIG. 1 is a plan view showing one embodiment of the humidity sensitive device of the present invention and FIG. 2 is a sectional view showing another embodiment of the present invention.

Referring to FIG. 1, the device of the invention comprises a device body 11 made of a semiconductive ceramic, a pair of comb shaped electrodes 12 and 13 formed on the major surface of the device body 11 and lead terminals 14 and 15 for external connection of the electrodes 12 and 13.

Referring to FIG. 2, the inventive device comprises a device body 21 made of a semiconductive ceramic, paired porous electrodes 22 and 23 formed on the respective opposing surfaces of the device body 21 so as to be opposed to each other, and lead terminals 24 and 25 for external electrical connection of the electrodes 22 and 23.

The semiconductive ceramic of the device body 11 or 21 comprises a grain boundary, and a high resistance layer having a humidity sensitive function is formed in the above described grain boundary.

In the FIG. 1 embodiment, the initial resistance value can be determined by selecting the spacing between the electrodes, the overlapping lengths of the electrodes, and the like. On the other hand, the FIG. 2 embodiment has an initial resistance value which is largely dependent on the thickness of the device body 21. Since the thickness of the device body 21 cannot be much decreased in consideration of the strength of the ceramic body, in general the FIG. 2 embodiment has a relatively high initial resistance value as compared with the FIG. 1 embodiment.

The electrodes 22 and 23 formed on the body 21 of the FIG. 2 embodiment may be formed on the whole surfaces or may be formed to expose a portion of the major surfaces of the device body 21 in consideration of the humidity absorbing capability of the device body 21.

In a preferred embodiment of the present invention, the high resistance layer having the above described humidity sensitive function may be formed by oxidizing the grain boundary or by reacting ions on the grain boundary for controlling the humidity sensing characteristics thereof.

Generally, is well-known, the above described semiconductive ceramic may be obtained; (1) by doping in $BaTiO_3$ an impurity such as $Bi_2O_3$, $Nb_2O_5$, $Sb_2O_5$, and a rare earth compound such as $Y_2O_3$, $CeO_2$, $La_2O_3$ or the like; (2) by doping in $BaTiO_3$ an impurity such as $Bi_2O_3$, $Nb_2O_5$, $Sb_2O_5$, and a rare earth compound such as $Y_2O_3$, $CeO_2$, $La_2O_3$ or the like and then sintering the same in a reducing atmosphere; or (3) by sintering $BaTiO_3$ in a reducing atmosphere. $SrTiO_3$, $MgTiO_3$, $TiO_2$ $CaTiO_3$ or the like may be used in place of $BaTiO_3$ as the semiconductive ceramic for the purpose of the present invention. In order to provide such semiconductive ceramics with porosity as described above, it has been found that it suffices to increase above normal the amount of the binder used in forming the ceramic before sintering.

In the following, several examples embodying the present invention will be described.

EXAMPLE 1

Figure 3:
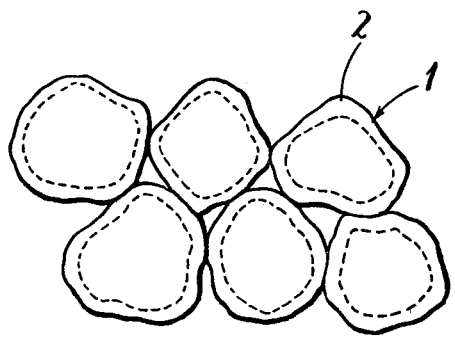
FIG. 3 is an enlarged diagrammatic view showing grains of a semiconductive ceramic of a further embodiment of the invention.
Figure 4:
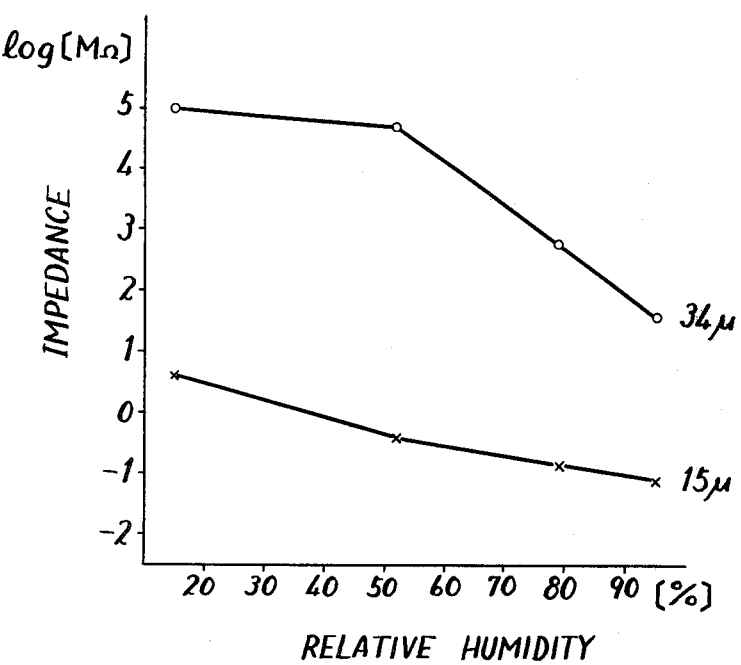
FIG. 4 is a graph showing the impedance/humidity characteristic of the embodiment of FIG. 3.

FIGS. 3 and 4 are views for explaining example 1, wherein FIG. 3 is an enlarged diagrammatic view showing the grain boundary of the semiconductive ceramic and FIG. 4 is a graph showing the impedance/humidity characteristic of the device of Example 1.

$SrTiO_3$ powder doped with $Y_2O_3$ of 0.5 mol% is admixed with cellulose powder of 3 wt%. The mixture is fully blended and formed into a pellet. The pellet is baked for two hours in a reducing atmosphere at 1400° C., and is then sintered to provide a ceramic disk of 8 mm in diameter and 0.4 mm in thickness.

By heating the ceramic disk thus obtained in air at 1000° C., the surface of the crystals is reoxidized. FIG. 3 shows the state of the surfaces of the grain boundary 1 where oxide layers 2 have been formed. By prolonging the heating period for reoxidation, the thickness of the oxide layer 2 is increased. Two different samples having oxide layers 2 of different thicknesses were fabricated. The thickness of the oxide layer 2 is presumed to be $34\mu$ for the first sample, and $15\mu$ for the second sample judging from the dielectric constant.

Gold electrodes were formed on the major surfaces of the above described respective samples with the spacing of 2 mm, and a voltage of 1 V AC (60 Hz) was applied between the electrodes to measure the change of the impedance therebetween with respect to the humidity. The result of the measurement is shown in FIG. 4. As seen from FIG. 4, the impedance value can be adjusted by changing the thickness of the oxide layer 2. The second sample having the oxide layer 2 of $15\mu$ in thickness exhibits a more linear proportional relation as compared with the first sample having the oxide layer 2 of $34\mu$ in thickness. Thus, it is observed that the thinner the oxide layer 2 the better the linearity of the proportional relation.

EXAMPLE 2

Figure 5:
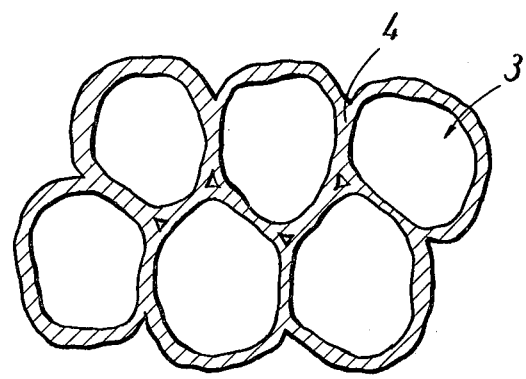
FIG. 5 is an enlarged diagrammatic view showing grains of the semiconductive ceramics of a further embodiment of the invention.
Figure 6:
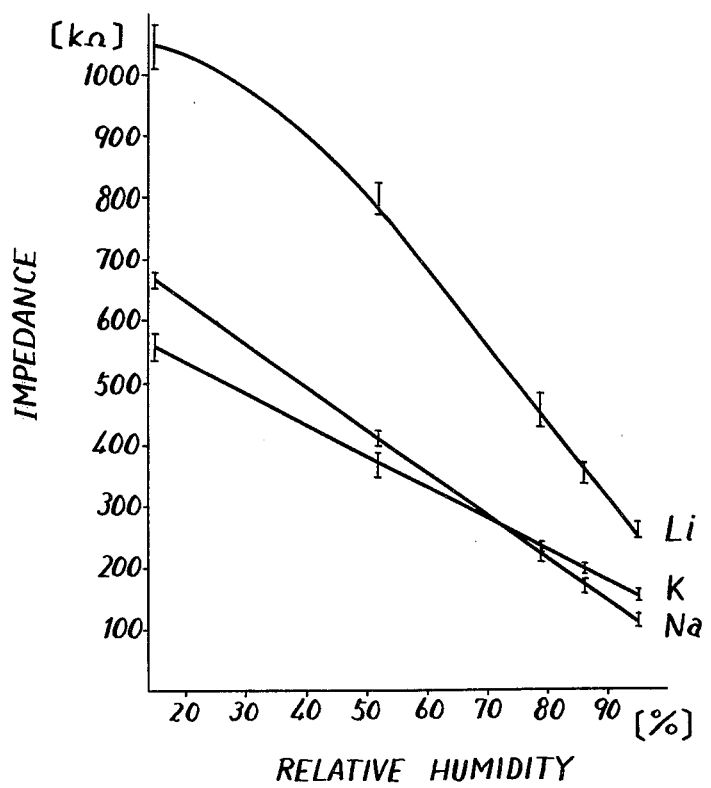
FIG. 6 is a graph showing the impedance/humidity characteristic of the embodiment of FIG. 5.
Figure 7:
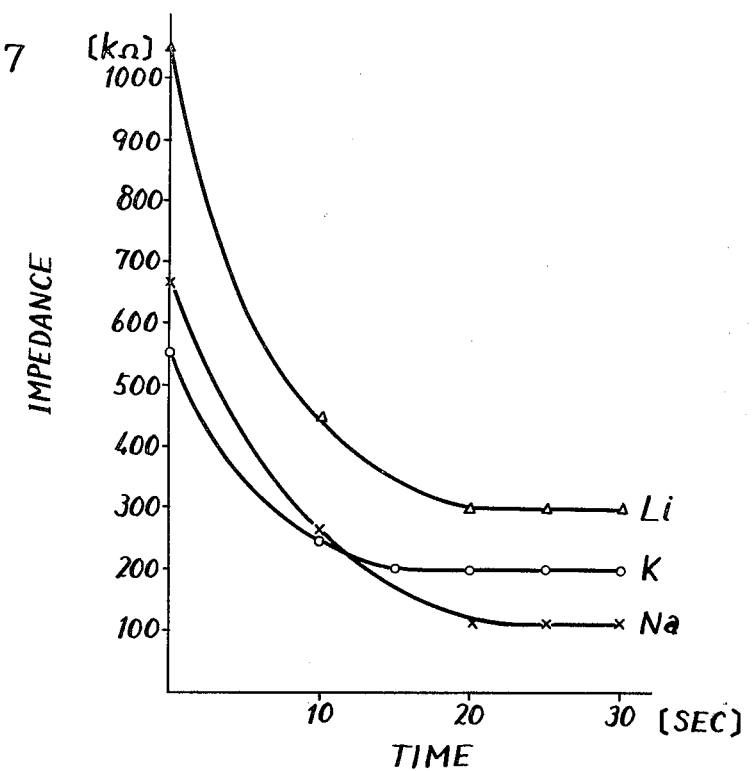
FIG. 7 is a graph showing the response rate characteristic of the embodiment of FIG. 5.

FIGS. 5 to 7 are views for explaining the example 2, wherein FIG. 5 is an enlarged diagrammatic view of the grain boundary of the semiconductive ceramics, FIG. 6 is the impedance/humidity characteristic of the example 2 and FIG. 7 is a graph showing an impedance response rate with respect to the humidity.

$SrTiO_3$ powder doped with $Y_2O_3$ of 0.5 mol% is admixed with cellulose powder of 20 wt% and is well blended, and then is formed into a pellet. The pellet is then fired for two hours in a reducing atmosphere at 1400° C., and is baked, thereby to provide a ceramic disk of 16.5 mm in diameter and 0.4 mm in thickness.

The ceramic disk thus obtained is coated with a water solution of alkali carbonate, so that 0.9 mg of alkali carbonate of is absorbed. The alkali carbonate may be a carbonate of alkali metals such as Li, Na, K, Rb or Cs. The ceramic disk with the alkali carbonate absorbed is heated for an hour in air at 1000° C., whereby the alkali metal ions are diffused as an dopant in the grain boundary of the semiconductive ceramic. FIG. 5 shows the grain boundary 3 of the semiconductor ceramics, with the dopant diffused, whereby an impurity layer 4 serving as a high resistance layer is formed in the grain boundary 3.

Comb shaped electrodes are formed with the electrode spacing of 0.6 mm and the electrode overlapping length of 1.8 cm on the major surfaces of the samples thus obtained. A voltage of 1 V AC (60 Hz) is applied between the electrodes, whereupon the impedance was measured. FIG. 6 is the result of measurement of the impedance with respect to humidity.

FIG. 6 simultaneously shows the characteristics of samples employing Li, Na and K as the alkali metal of the above described alkali carbonate. FIG. 6 shows the variation range of the impedance value by line segments extending in the vertical direction, each line segment showing a variation change within three months. As is clear from FIG. 6, a stable reproducibility is attained.

FIG. 7 shows a time dependent change of the impedance when the relative humidity is changed from 15% to 95% in the case of the above described samples. As is clear from FIG. 7 the impedance value reaches a balanced state in approximately 18 to 20 seconds, which indicates a quick response rate.

EXAMPLE 3

Figure 8:
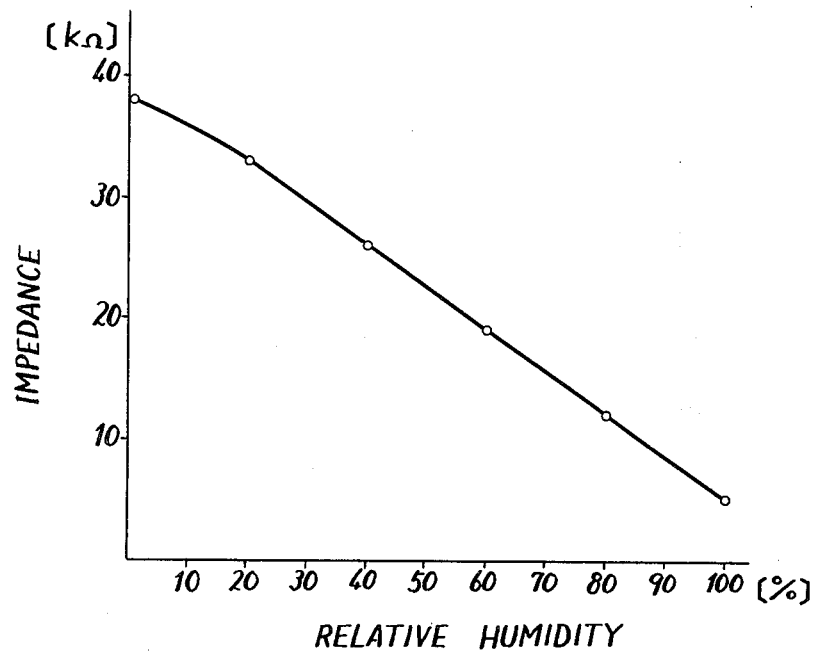
FIg. 8 is a graph showing the impedance/humidity characteristic of yet a further embodiment of the invention.

FIG. 8 is a graph showing the impedance/humidity characteristic of a third example.

$BaTiO_3$ powder doped with $CeO_2$ of 0.3 mol% is admixed with cellulose powder of 14 wt% and the mixture is fully blended. The mixed material is then molded by a press into a disk of 12 mm in diameter and 1.1 mm in thickness. The molded disk is then fired for an hour at 1250° C., whereupon the fired unit is polished to the thickness of $300\mu$ and is then cleansed and dried. A conductive paste is coated on both surfaces of the polished unit by a screen process in a layer of 8 mm in diameter. Then for the purpose of reoxidation processing and baking of the conductive paste, the unit is heat treated at the temperature of 900° C. Then lead wires are soldered to the porous electrodes thus obtained, thereby to complete a humidity sensitive device as shown in FIG. 3. A voltage of 1 V AC (60 Hz) is applied between the electrodes, whereupon the impedance is measured at various relative humidity.

Since the inventive humidity sensitive device comprises a semiconductive ceramic as a device body, the device exhibits less time dependent deterioration of the characteristic and exhibits a stable operation characteristic. Furthermore, the sensitivity and the device resistance can be changed with ease by changing the thickness of the high resistance layer formed on the grain boundary of the semiconductive ceramic and by changing the kinds of ions for reaction, which permits manufacture of a device suitable for any application. Since the semiconductive ceramic itself also has an inherent resistance value, the characteristics of the device can also be predetermined by changing the material of the semiconductive ceramic. Thus, the inventive device is easy to miniaturize, simple to produce and inexpensive. In the past it was difficult to fabricate a ceramic humidity sensitive thin film with a thickness of only several tens of microus; however the humidity sensitive device of the invention having a ceramic humidity sensitive thin film can be provided with ease by oxidation of the surface of the grain boundary or by diffusion reaction of ions. In addition, a humidity sensitive device having a quick humidity sensitive response rate is provided. Furthermore, a humidity sensitive device having a relatively low resistance such as several $\Omega$ to several million $\Omega$ is provided which can be advantageously utilized in circuit designing. It has been observed that the smaller the device resistance the less noise is generated by the device. It has also been observed that the smaller the device resistance the less resistance variation due to contamination of the device occurs.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A humidity sensitive device, comprising:
   a device body comprising a semiconductive ceramic, said semiconductive ceramic having a grain boundary;
   a high resistance layer formed in said grain boundary of said semiconductive ceramic, the electrical impedance of said high resistance layer varying as a function of humidity; and
   electrode means formed on said device body in electrical contact with said high resistance layer.

2. A humidity sensitive device in accordance with claim 1, wherein said high resistance layer comprises an oxide layer obtained by oxidation of said grain boundary of said semiconductive ceramic.

3. A humidity sensitive device in accordance with claim 2, wherein said electrode means comprises a baked conductive paste, and wherein said oxide layer obtained by oxidation of said grain boundary of said semiconductive ceramic is formed simultaneously with said electrode means.

4. A humidity sensitive device in accordance with claim 1, wherein said high resistance layer comprises an impurity layer obtained through reaction of ions on said grain boundary of said semiconductive ceramic.

5. A humidity sensitive device in accordance with claim 1, wherein said semiconductive ceramic comprises a ceramic doped with an impurity.

6. A humidity sensitive device in accordance with claim 1, wherein said semiconductive ceramic comprises a chemically reduced ceramic.

7. A humidity sensitive device in accordance with claim 1, wherein said semiconductive ceramic comprises a ceramic doped with an impurity and then chemically reduced.

8. A humidity sensitive device in accordance with claim 1, wherein said device body has a first major surface, said electrode means comprising first and second electrodes disposed on said major first surface and spaced apart from each other.

9. A humidity sensitive device in accordance with claim 1, wherein said device body has first and second opposed major surfaces, said electrode means comprising first and second electrodes disposed respectively on said first and second major surfaces.

10. A humidity sensitive device in accordance with claim 1, wherein said semiconductive ceramic comprises a member of the group consisting of $BaTiO_3$, $SrTiO_3$, $MgTiO_3$, $TiO_2$ and $CaTiO_3$.

11. A humidity sensitive device in accordance with claim 5 or claim 7, wherein said semiconductive ceramic comprises a member of the group consisting of $BaTiO_3$, $SrTiO_3$, $MgTiO_3$, $TiO_2$ and $CaTiO_3$; said impurity including a first dopant from the group consisting of $Bi_2O_3$, $Nb_2O_5$ and $Sb_2O_5$ and a second dopant selected from the group of $Y_2O_3$, $CeO_2O_3$.

12. A method for manufacturing a humidity sensitive device, said method comprising the steps of:
   providing a device body comprising a semiconductive ceramic which has a grain boundary;
   forming a high resistance layer in said grain boundary; said high resistance layer having an electrical impedance that varies as a function of humidity; and
   disposing electrode means on said device body in electrical contact with said high resistance layer.

13. A method according to claim 12, wherein said step of forming said high resistance layer comprises oxidizing said grain boundary to form an oxide layer.

14. A method according to claim 13, wherein said step of disposing said electrode means on said device body comprises baking a conductive paste thereon.

15. A method according to claim 14, wherein said oxidizing step and said baking step are performed simultaneously.

16. A method according to claim 12, wherein said step of forming said high resistance layer comprises reacting ions of an impurity on said grain boundary.

17. A method according to claim 12, wherein said step of providing said device body comprises the step of doping said semiconductor ceramic with an impurity.

18. A method according to claim 17, wherein said step of providing said device body comprises selecting said semiconductor ceramic from the group consisting of $BaTiO_3$, $SrTiO_3$, $MgTiO_3$, $TiO_2$ and $CaTiO_3$.

19. A method according to claim 18, wherein said step of doping said semiconductor ceramic comprises doping it with a first dopant selected from the group of $Bi_2O_3$, $Nb_2O_5$ and $Sb_2O_5$ and further comprises doping it with a second dopant selected from the group of $Y_2O_3$, $CeO_2$ and $La_2O_3$.

20. A method according to claim 19, wherein said semiconductive ceramic comprises $BaTiO_3$ and said second dopant comprises $CeO_2$, said step of doping said semiconductive ceramic comprising mixing said $BaTiO_3$ with said $CeO_2$ to form a mixture and baking said mixture at 1250° C.

21. A method according to claim 19, wherein said semiconductive ceramic comprises $SrTiO_3$ and said second dopant comprises $Y_2O_3$, and wherein said step of doping said semiconductive ceramic comprises mixing said $Y_2O_3$ with said $SrTiO_3$ to form a mixture and baking said mixture at 1400° C. in a reducing atmosphere to form a solid body.

22. A method according to claim 21, wherein said step of providing said device body further comprises coating at least a portion of said solid body with a water solution of an alkali carbonate and thereafter baking it at 1000° C.

23. A method according to claim 22, wherein said alkali carbonate is a carbonate of one of the group of lithium, sodium and potassium.

24. A method according to claim 17, wherein said step of providing said device body comprises the steps of chemically reducing said semiconductive ceramic after it has been doped with said impurity.

* * * * *